US010287636B2

(12) United States Patent
Hillebrand et al.

(10) Patent No.: US 10,287,636 B2
(45) Date of Patent: *May 14, 2019

(54) METHOD AND RAPID TEST FOR THE DETECTION OF SPECIFIC NUCLEIC ACID SEQUENCES

(71) Applicant: AJ INNUSCREEN GmbH, Berlin (DE)

(72) Inventors: Timo Hillebrand, Hoenow (DE); Elmara Graser, Berlin (DE)

(73) Assignee: AJ INNUSCREEN GmbH, Berlin (DE)

( * ) Notice: Subject to any disclaimer, the term of this patent is extended or adjusted under 35 U.S.C. 154(b) by 820 days.

This patent is subject to a terminal disclaimer.

(21) Appl. No.: 14/299,674

(22) Filed: Jun. 9, 2014

(65) Prior Publication Data

US 2015/0024386 A1  Jan. 22, 2015

Related U.S. Application Data

(63) Continuation of application No. 12/644,982, filed on Dec. 22, 2009, now abandoned, which is a continuation of application No. PCT/EP2008/057857, filed on Jun. 20, 2008.

(30) Foreign Application Priority Data

Jun. 22, 2007 (DE) .......................... 10 2007 029 772

(51) Int. Cl.
*C12Q 1/68* (2018.01)
*C12Q 1/689* (2018.01)

(52) U.S. Cl.
CPC ....... *C12Q 1/689* (2013.01); *C12Q 2600/158* (2013.01)

(58) Field of Classification Search
CPC ...................................................... C12G 1/68
See application file for complete search history.

(56) References Cited

U.S. PATENT DOCUMENTS

| | | | | |
|---|---|---|---|---|
| 5,525,494 A * | 6/1996 | Newton | ........... | C07H 21/00 435/91.2 |
| 5,804,380 A | 9/1998 | Harley et al. | | |
| 5,955,351 A * | 9/1999 | Gerdes | ........... | B01L 3/502 422/112 |
| 6,037,127 A * | 3/2000 | Ebersole | ........... | C12Q 1/6816 435/6.19 |
| 7,087,414 B2 * | 8/2006 | Gerdes | ........... | C12Q 1/6827 435/91.1 |
| 7,749,772 B1 | 7/2010 | Wang | | |
| 2003/0143580 A1 | 7/2003 | Straus | | |
| 2003/0224437 A1 * | 12/2003 | Gerdes | ........... | C12Q 1/6827 435/6.12 |
| 2005/0227275 A1 * | 10/2005 | Jung | ........... | C12Q 1/6816 435/6.16 |
| 2005/0260124 A1 | 11/2005 | Yamada et al. | | |
| 2007/0054296 A1 * | 3/2007 | Piepenburg | ........... | C12Q 1/6816 435/6.13 |
| 2009/0148847 A1 * | 6/2009 | Kokoris | ........... | B01F 11/0071 435/6.14 |
| 2009/0148849 A1 * | 6/2009 | Galvan-Goldman | ........... | C12Q 1/6858 435/5 |
| 2010/0099099 A1 | 4/2010 | Graser et al. | | |
| 2010/0291666 A1 * | 11/2010 | Collier | ........... | B01L 3/502715 435/287.2 |
| 2010/0330574 A1 * | 12/2010 | Whitman | ........... | C12Q 1/6853 435/6.1 |
| 2013/0115597 A1 | 5/2013 | Graser et al. | | |

FOREIGN PATENT DOCUMENTS

| | | |
|---|---|---|
| WO | WO 2004/011612 | 2/2004 |
| WO | WO 2004/065010 | 8/2004 |
| WO | WO 2004099438 | 11/2004 |
| WO | WO 2006/041524 | 4/2006 |

OTHER PUBLICATIONS

Kozwich et al. (Development of a novel, rapid integrated Cryptosporidium parvum detection assay, Appl Environ Microbiol. Jul. 2000;66(7):2711-7).*
Wang et al. (A disposable microfluidic cassette for DNA amplification and detection, Lab Chip, 2006,6, 46-53, Dec. 5, 2005).*
Glynou et al. (Oligonucleotide-functionalized gold nanoparticles as probes in a dry-reagent strip biosensor for DNA analysis by hybridization, Anal Chem. Aug. 15, 2003;75(16):4155-60).*
Carter et al. (Lateral flow microarrays: a novel platform for rapid nucleic acid detection based on miniaturized lateral flow chromatography, Nucleic Acids Res. 2007;35(10):e74. Epub May 3, 2007).*
U.S. Appl. No. 13/639,774, filed Jan. 15, 2013, US2013/0115597 A1, Graser ,et al.
U.S. Appl. No. 12/559,252, filed Sep. 14, 2009, US2010/0099099 A1, Graser ,et al.
Andrew O. Crockett, et al., Fluorescein-Labeled Oligonculeotides for Real-Time PCR: Using the Inherent Quenching of Deoxyguanosine Nucleotides, Analytical Biochemistry, vol. 290, pp. 89-97, 2001.

(Continued)

*Primary Examiner* — Aaron A Priest
(74) *Attorney, Agent, or Firm* — Grüneberg and Myers PLLC

(57) ABSTRACT

A universally usable method for specific detection of target nucleic acid sequences, which method can be performed very rapidly and also simply and furthermore which does not need any expensive instrumental systems. The method is intended to be suitable as a molecular genetic rapid test and to respect the requirements of diagnostic specificity assurance. In this regard it is important that only one specific amplification product be detected and that amplification artifacts can be unambiguously discriminated. A nucleic acid amplification kit suitable for performing this method.

23 Claims, 3 Drawing Sheets
Specification includes a Sequence Listing.

(56) References Cited

OTHER PUBLICATIONS

"9$^{th}$ Congress of Infectious Diseases and Tropical Medicine", Infection; A Journal of Infectious Disease, Urban & Vogel, MU, vol. 36, No. 1, Feb. 19, 2008, pp. 1-82 w/abstracts, XP019583475.
Carl T. Wittwer, et al., "Real-Time Multiplex PCR Assays", Methods 25, pp. 430-442 (2001).
Kenneth E. Pierce, et al., "Linear-After-The-Exponential Polymerase Chain Reaction and Allied Technologies", Methods in Molecular Medicines: Single Cell Diagnostics, Jun. 15, 2007, pp. 65-85.
Amodia Bioservice GmbH: "Gebrauchsanweisung Genflow Borrelia Plus", Package Insert, Mar. 7, 2006, pp. 1-12.
Hermann et al. (Nov. 2004) Ultrafast DNA Amplification With a Rapid PCR System. Article in Biotech on line 4 pages.
Kozwich et al. (2000) Applied and Environmental Microbiology, vol. 66, No. 7, pp. 2711-2717.
O'Connor (2003) Methods in Molecular Biology, Humana Press Totowa, NJ, vol. 216, pp. 185-192.

\* cited by examiner

METHOD AND RAPID TEST FOR THE DETECTION OF SPECIFIC NUCLEIC ACID SEQUENCES

CROSS-REFERENCE TO RELATED APPLICATIONS

This application is a continuation of PCT/EP2008/057857, filed Jun. 20, 2008, and claims priority to Germany 10 2007 029 772.8, filed Jun. 22, 2007, both of which are hereby incorporated by reference.

BACKGROUND OF THE INVENTION

Field of the Invention

The present invention relates to a method and a test kit for detection of specific nucleic acid sequences with the steps of amplification, hybridization by means of probes, and detection of the hybridization event; wherein the detection of the hybridization event takes place on a solid phase outside the reaction vessel for amplification/hybridization.

Description of the Related Art

Genetic diagnostics has become an indispensable tool of modern medical laboratory diagnostics, forensic diagnostics, veterinary medical laboratory diagnostics or food and environmental diagnostics.

Genetic diagnostics was revolutionized with the invention of PCR technology, with which it is possible to amplify any arbitrary nucleic acid sequence specifically.

The use of PCR covers a diversity of methods, which in combination with the PCR technology additionally permit specific detection of completed amplification. Especially the requirements of an exact genetic diagnosis must make use of methods that ensure that a generated amplification product also corresponds to the target sequence that is specifically to be detected. The widespread use of visualization of a PCR product by means of gel electrophoresis is not sufficient for this purpose.

One possibility for detection of specific nucleic acid sequences in a way that in principle can be achieved very rapidly and without great experimental time and effort is what are known as real-time PCR methods. In this case the amplification reaction is directly coupled with the actual detection reaction.

A widely used method for detection of specific nucleic acids is light cycler technology (Roche). For this purpose Roche has developed special hybridization probes, consisting of two different oligonucleotides, each labeled with only one fluorochrome. The acceptor is located at the 3'-end of the one probe and the other oligonucleotide has a donor at the 5'-end. The probes are chosen such that they both bind to the same DNA strand, the distance between acceptor and donor being permitted to be at most 1 to 5 nucleotides, so that what is known as the FRET effect can occur. The fluorescence is measured during the annealing step, in which only light of this wavelength is detectable as long as both probes are bound to the DNA. In this system the melting point of both probes should be identical. Because of the use of two hybridizing probes in addition to the primers used, the specificity of this detection system is extremely high.

A further real-time PCR application for detection of specific nucleic acid targets can be performed with what are known as double-dye probes, which are disclosed in U.S. Pat. Nos. 5,210,015 and 5,487,972 (TaqMan probes), both of which are incorporated by reference. Double-dye probes carry two fluorochromes on one probe. The reporter dye is located in this case at the 5'-end and the quencher dye at the 3'-end. In addition, a phosphate group is also located at the 3'-end of the probe if necessary, so that the probe cannot function as a primer during elongation. As long as the probe is intact, the released light intensity is low, since almost the entire light energy produced after excitation of the reporter is absorbed and transformed by virtue of the spatial proximity of the quencher. The emitted light of the reporter dye is "quenched", or in other words extinguished. This FRET effect is preserved even after the probe has bonded to the complementary DNA strand. During the elongation phase, the polymerase encounters the probe and hydrolyzes it. The ability of the polymerase to hydrolyze an oligonucleotide (or a probe) during strand synthesis is known as 5'-3' exonuclease activity. Not all polymerases have 5'-3' exonuclease activity (Taq and Tth polymerase). This principle was first described for the Taq polymerase. The principle is known as the TaqMan principle. After probe hydrolysis, the reporter dye is no longer located in spatial proximity to the quencher. The emitted fluorescence is now no longer transformed and this fluorescence increase is measured.

A further option for specific detection of amplification products by means of real-time PCR technology consists in the use of intercalating dyes (ethidium bromide, Hoechst 33258, Yo-Pro-1 or SYBR Green™ and the like). After being excited by high-energy UV light, these dyes emit light in the lower-energy visible wavelength region (fluorescence). If the dye is present as a free dye in the reaction mixture, the emission is very weak. Only by intercalation of the dye, whereby it fits into the small furrows of double-strand DNA molecules, is the light emission greatly intensified. The dyes are inexpensive and universally usable, since in principle any PCR reaction can be followed in real time with them. In addition, they have high signal strength, since every DNA molecule binds several dye molecules. From the advantages, however, there also results an extreme disadvantage for application: In principle it is not possible by means of intercalating dyes to distinguish between correct product and amplification artifacts (such as primer dimers or defective products). While primer dimers and other artifacts are being formed, they naturally also bind intercalating dyes and thus lead to an unspecific increase in fluorescence even in negative samples. However, a clear differentiation between specific amplification event or artifact is absolutely necessary. In order to achieve this in any case, what is known as a melting-point analysis is performed at the end of the actual PCR reaction. For this purpose the reaction mixture is heated in steps of 1 degree from 50° C. to 90° C. The fluorescence is measured continuously during this process. The point at which double-strand DNA melts is characterized by a decrease (peak) of the fluorescence of the intercalating dye, since the intercalating dye dissociates from the single-strand DNA. When the PCR is optimally adjusted, a melting-point peak that tapers sharply is to be expected. This melting point represents the specific product to be expected. Products of different sizes and products of other sequences have different melting points.

When the fluorescence is plotted graphically against temperature, the fluorescence decrease of the two products can be perceived as two separate melting points. Thus this system gains specificity and makes it possible to distinguish a specific amplification product from artifacts. In this way it is possible to distinguish even between homozygotes (single peak) and heterozygotes (two peaks).

Furthermore, it is also possible to achieve quantitation of the targets to be detected by means of REAL-time PCR applications.

As already explained, the described methods fulfill the need for specific detection of an amplification product.

A great disadvantage, however, is that they are implemented on very expensive instrumental platforms, which have to unite the process of amplification and that of subsequent optical detection, in a manner corresponding to the problem, in one hardware solution. Furthermore, many of these described detection methods are still based on real-time tracking of the amplification process. On the basis of this strategy, even workup of the measured fluorescence values takes place in the course of the amplification reaction. It is clear to those skilled in the art that, in this connection, an enormously large body of analysis algorithms must also be integrated into real-time systems. Ultimately this explains the high financial expenditure that must be invested for the use of real-time PCR systems, Also ultimately, the operation of such instrumental systems requires a high degree of expertise.

Besides the described diagnostic detections based on REAL-time PCR, however, alternative variants for specific detection of nucleic acids also exist.

An example of less expensive methods for detection of nucleic acids in this connection is PCR-ELISA. In this method, the DNA sequence to be examined is amplified and the generated DNA fragment is then covalently immobilized on a solid phase (such as microtiter plates or strips), denatured to a single strand and hybridized with a sequence-specific probe. Successful binding of the probe can be visualized with an antibody-mediated color reaction. Another variant is based on immobilizing the probes on a solid phase, denaturing the PCR product and then bringing it into contact with the immobilized probe. Detection of a completed hybridization event takes place by analogy with the first variant of the method.

In principle, PCR-ELISA methods are easy to perform, but they comprise multiple procedural steps. Besides the time needed to perform the PCR, therefore, several hours of working time are also needed to perform the subsequent detection method. Such a method usually needs 8 hours and therefore is also not suitable as a rapid test.

Furthermore, some items of equipment are also needed, such as a temperature-control station, what is known as a washer, or even a measuring instrument for detection of the hybridization signal. Furthermore, other special instruments or special consumable materials may also be necessary.

Further simple methods for detection of amplification products are based on amplification of the target sequences and subsequent hybridization of amplification products on a membrane. These methods also have several variants known to those skilled in the art. Once again, however, these methods are also laborious to perform, need a large number of procedural steps to be performed and therefore are not suitable as rapid tests. This then also applies to the use of biochip strategies, which use hybridization of PCR products with hybridization probes for detection of the specificity. These methods also are laborious and associated with very expensive instrumental platforms.

A distinct reduction of working steps is disclosed in Korean Patent 1020060099022 A (Method and kit for rapid and accurate detection and analysis of nucleotide sequence with naked eye by using membrane lateral flow analysis).

In this case what is known as a lateral flow method is used to detect nucleic acids. This method also makes use of the technology of hybridization of nucleic acids on a solid phase. Advantageously, a lateral flow method has a small, handy test format (strip test).

In contrast to the above patent specification, a very fast detection method, which also makes use of detection of amplification products by means of a test strip and is commercially available, is in turn based on a completely different principle. In this case the PCR reaction is performed with a biotinylated primer and a non-biotinylated primer. After the PCR has been performed, there is obtained a PCR product that is therefore biotin-labeled at one end. Detection is achieved using a test strip (for example of the Millenia Co.), which contains two separate binding sites: a streptavidin site for coupling the biotin-labeled DNA strand and an FITC binding site for functional control of the test strip.

Detection of the PCR product is achieved by denaturing the PCR mixture on completion of the PCR and hybridizing it with a probe complementary to the biotin-labeled DNA strand. The probe is FITC-labeled.

For detection, the PCR mixture is mixed with a running buffer and applied on the test strip. According to the description of the test, the biotinylated DNA strand binds to the streptavidin binding site of the strip. Detection takes place via the FITC labeling of the probe hybridized with the DNA strand. A typical signal in the form of a strip is developed. This signal is supposed to be the specific detection of the amplification product. However, the method does not combine hybridization of the probe with the PCR process but instead performs the latter process as a separate procedural step. However, the method suffers from a fundamental and dramatic error source.

Detection of the target nucleic acid to be detected is not specific. The reason is that artifacts such as primer dimers are formed during PCR and naturally also bind specifically to the streptavidin binding sites of the test strip, and so they can cause a positive reaction just as does a specific PCR product.

International Document WO 2004/092342 A2 describes the technology of the lateral-flow assay, which is incorporated by reference. As examples of application to molecular biology, there are used already known and in some cases commercially available technologies, which are adapted to the lateral-flow assay of that invention. In Example 1 of WO 2004/092342 A2, one of the RT reactions and subsequent amplification is performed with two labeled primers. This method may lead to false-positive results due to primer-dimer formation and mispriming. The second option (FIG. 20d-e) represents a subsequent hybridization with two labeled probes. The problem of primer-dimer formation and mispriming is not acknowledged in that publication.

The important problem of false-positive results due to primer-dimer formation was correctly recognized in the publication of Kozwich, et al. (Development of a novel, rapid integrated *Cryptosporidium parvum* detection assay. Appl. Environ. Microbiol. (2000) 66 (7) 2711 7, page 2712, right column, $2^{nd}$ par., FIG. 3), incorporated by reference. The solution of the problem (nested PCR with the labeled and non-labeled primers) differs in principle from the solution of the present invention, for which protection is applied for herewith (one labeled primer and one labeled probe). The solution proposed in the publication of Kozwich, et al. excludes the formation of primer dimers only as a matter of probability but not of principle. The mispriming that occurs so often is also not completely excluded as an error source in the solution proposed by Kozwich, et al.

All of the described alternative methods for detection of nucleic acid sequences without REAL-time PCR technologies therefore also have a substantial common feature, regardless of the considerable manual working effort that is still necessary. The necessary hybridization reaction between PCR product and specific probe always takes place outside the PCR process. This feature is at the base of all of these methods. A major advantage of REAL-time PCR technologies, however, is precisely that the processes of amplification and specific hybridization take place in one reaction vessel, and so the processes of amplification and hybridization are not disconnected. Furthermore, amplification artifacts frequently lead to a false-positive signal in these cases.

BRIEF SUMMARY OF THE INVENTION

An objective of the present invention was to provide a universally usable method for specific detection of target nucleic acid sequences, which method can be performed very rapidly and also simply and furthermore which does not need any expensive instrumental systems. The method is intended to be suitable as a molecular genetic rapid test and to respect the requirements of diagnostic specificity assurance. In this regard it is important that only one specific amplification product be detected and that amplification artifacts can be unambiguously discriminated.

DETAILED DESCRIPTION OF THE INVENTION

Figure 1:
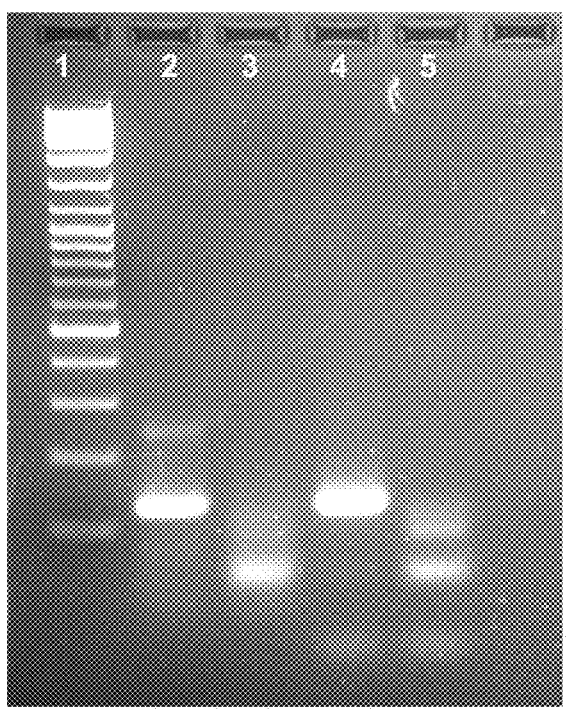
FIG. 1 shows the amplification event/the hybridization reaction as detected by means of gel-electrophoretic separation of the amplification/hybridization mixture. Lane 1: DNA ladder; lane 2: positive control containing *L. monocytogense* DNA from mixture 1 containing sense primer, antisense primer, probe, dNTP Mix, 10×PCR buffer, Taq-DNA polymerase and PCR-grade $H_2O$; lane 3: negative control from mixture 1; lane 4: positive control containing *L. monocytogense* DNA from mixture 2 containing sense primer, antisense primer, probe, dNTP Mix, 10×PCR buffer, Taq-DNA polymerase and PCR-grade $H_2O$; lane 5: negative control from mixture 2.

This object and others were achieved as described below. Conventional PCR procedures, including amplification and hybridization steps are well-known and are incorporated by reference to the publications described above. The significant conceptual and technical problems inherent to conventional methods, such as those described above, were solved by the inventors as described below.

Herein the present invention solves the existing problem in the most ideal way. Furthermore, the inventive method for the first time combines the amplification reaction and specific probe hybridization in one and the same reaction vessel and is nevertheless able to dispense completely with the extremely expensive instrumental systems of REAL-time PCR.

The inventive method for detection of specific nucleic acid sequences is based on a probe hybridization integrated into the PCR, followed by simple detection of the specific hybridization event. This detection takes place outside the PCR reaction vessel. Preferably there is used, for example, a lateral-flow technology (detection strips). Thus the test procedure now needs nothing more than one PCR apparatus and one test strip and can be performed simply, extremely rapidly and without problems, even by unskilled personnel. In a preferred alternative embodiment, the rapid-cycler technology (patent) is used. The combination of rapid PCR and detection strips makes it possible to perform the test for detection of a specific nucleic acid in not even one hour and to do so for extremely low test costs.

This inventive method is based on the following steps:
A. Preparation of a PCR Reaction Mixture Comprising:
1. two PCR primers, one of the primers being labeled at the 5'-end with a labeling molecule (such as biotin)
2. a specific hybridization probe (also provided with labeling; for example FITC), which is able to hybridize to the strand of the target sequence containing the labeled primer
3. PCR reagents known in themselves: PCR buffers, polymerases, dNTPs and if necessary further additives.

B. Performance of the Amplification Process with Integrated Probe Hybridization

The amplification reaction takes place under standard conditions. The actual amplification reaction is followed by a denaturing step at a temperature of >90° C. for thermal separation of the strands of the amplification product generated during the PCR. After denaturing, the PCR reaction mixture is cooled to the hybridization temperature of the probe. During this step the hybridization probe binds specifically to the complementary DNA strand of the amplification product. This strand then contains the biotin labeling, which was incorporated by the biotin-labeled primer into the PCR product.

C. Detection of the Hybridization Event

Detection of the specific hybridization event takes place via specific coupling of the biotinylated DNA strand to a solid phase and specific detection of the label of the hybridization probe, which is hybridized to the sequence of the biotinylated DNA strand complementary to the probe. In a preferred variant, commercially available lateral-flow test strips (for example, from Millenia) are used for detection. As already explained, the test strip contains two separate binding sites: a streptavidin site for coupling the biotin-labeled label and an FITC binding site for functional control of the test strip. For detection, the PCR mixture is mixed with a running buffer and applied on the test strips. The following binding events may occur.

1. In the lower zone of the test strip, where the sample is applied, all FITC-labeled nucleic acids (non-hybridized FITC-labeled hybridization probe or hybridization product between biotin-labeled DNA strand and FITC-labeled hybridization probe) bind to gold particles, which are coated with anti-FITC antibodies.
2. The streptavidin binding site is located further along the test strip. The following nucleic acids are able to bind to this binding site: 1. the biotin-labeled primer, 2. the biotin-labeled DNA strands and 3. the products of hybridization between biotin-labeled DNA strand and FITC-labeled hybridization probe.

However, a detection signal is able to be visible only when the specific hybridization product between biotin-labeled DNA strand and FITC-labeled hybridization probe exists, since only this product is also coupled to the detection system (FITC/anti-FITC gold particles).

3. Further along the test strip, there then bind excess gold particles coated with anti-FITC antibodies, which serve as control of the functional capability of the test strip.

After the described method was performed (Practical example 1), it was possible to achieve detection of an amplification product without problems. However, it was found that the negative control conducted in parallel may also cause a strong positive test signal on the test strip. The following circumstance was discovered as the cause of the false-positive result. During the PCR, the FITC-labeled hybridization probe is also able to function as a primer. Thereby a shortened amplification product is formed and is therefore detected just as accurately as the specific amplification product would be. Such a result is not problematic in principle, since naturally it would also be specific. However, the problem is that amplification artifacts naturally are also formed when the hybridization probe acts as a primer. These primer dimers, which are so often formed, then lead on the test strip to a false-positive signal, since they bind specifically to the streptavidin site and are detected via the incorporated FITC label. This experimental result therefore shows that, in the described form, the detection probe cannot be integrated in the PCR mixture and thus the coupling of amplification and specific hybridization in one reaction vessel cannot function.

This may explain why a detection system of this type has not existed heretofore.

The inventive method surprisingly solves the problem by modifying the hybridization probe chemically such that it is no longer able to function as primer in the process of amplification, and so elongation by the polymerase is no longer possible. This is achieved by blocking the probe against the 5'→3' polymerase activity, preferably by phosphorylation of the last nucleotide of the probe. The process is further intensified by the fact that the melting temperature of the probe lies well below the temperatures at which the PCR takes place. By use of a modified probe it was possible to eliminate the described problem completely (see Practical example 1).

A further increase in efficiency of the test method can be achieved by modifying not only the described denaturing step after completion of the amplification reaction but also the PCR protocol. Thus, an increase of detection efficiency (higher signal strength on the test strip) is achieved by performing an asymmetric PCR (instead of the standard PCR reaction).

In summary, an extremely simple detection method is now available by virtue of the inventive method. The inventive integration of a hybridization probe into the PCR adds the certainty that the amplified fragment actually contains the target sequence. Thereby the false-positive results caused by mispriming are excluded. The use of the chemically modified probe (preferably phosphorylation of the last nucleotide of the probe) prevents elongation of the probe by 5'→3' polymerase activity, thus preventing the probe from functioning as a primer and generating unspecific PCR artifacts (primer dimers) that would be detected as false-positive signals.

In contrast to REAL-time PCR methods, the specific detection signal is not detected by means of fluorescence released by the probe hydrolysis caused by the Taq polymerase (EP 0972848 A2). Nevertheless, the advantage of real-time technologies is used, in that the PCR and hybridization take place in one reaction vessel, albeit not by quenching and exonuclease activity. The inventive method is also distinguished from that of a patent (EP 0826066 B1), which also represents a combination of PCR and hybridization. In this method also, a fluorescence signal mediated by FRET effect is again detected. This occurs during the amplification process by hybridization of a probe having a lower annealing temperature than does the primer. In this case, release of the fluorescence does not take place by hydrolysis of the probe as a result of exonuclease activity of the polymerase, but by the fact that the secondary structure of the probe becomes decomposed during hybridization, and so the fluorescence is less quenched. In this connection only enzymes having no exonuclease activity (such as Klenow fragment or T4 or T7 polymerases) can be used for amplification.

The fluorescence is always measured at the probe hybridization temperature. Thus, this method always needs extremely expensive real-time PCR instruments. As examples for final detection, the inventive method uses strips (lateral-flow formats) or other solid phases, which are easy to handle and which are capable of binding the DNA strand of the PCR product to be detected. The label of the probe is then detected by means of technologies known to those skilled in the art.

By means of the inventive method, an extremely simple, rapid and universal method is available for the first time for specific detection of an amplification event, and from the instrumentation viewpoint it needs only one PCR instrument. The combination of PCR and probe hybridization in one reaction vessel means that detection is now achieved merely by bringing the PCR reaction mixture into contact with the test strips. Thus the inventive method represents a test format that in principle can also be achieved under field conditions.

The inventive method will be explained hereinafter on the basis of practical examples, but the practical examples are not to be construed as any restriction of the method.

PRACTICAL EXAMPLES

Example 1

Detection of *Listeria monocytogenes* DNA by Means of the Hybridization Method Integrated into the PCR and of Lateral Flow Detection. Comparison of an Unphosphorylated and a Phosphorylated Probe.

Two types of labeled probes were tested against one another in the mixture. The first probe is FITC-labeled at the 5'-end, and the second probe is also singly phosphorylated at its 3'-end. The 3'-phosphorylation of the probe prevents it from being elongated by the Taq polymerase.

Mixture 1 (Unphosphorylated Hybridization Probe)
PCR Primer/Probe

```
L. monocytogenes sense primer
                                       (SEQ ID NO: 1)
(5'-CGC AAC AAA CTG AAG CAA AGG-3')

L. monocytogenes antisense primer
                                       (SEQ ID NO: 2)
(5'-BIOTIN-TCC GCG TGT TTC TTT TCG AT-3')

L. monocytogenes probe
                                       (SEQ ID NO: 3)
(5'-FITC-CCA TGG CAC CAC CAG CAT CT-3')
```

Reaction Mixture (Amplification/Hybridization)
Per sample:

| | |
|---|---|
| sense primer (50 pmol/µL) | 0.1 µL |
| antisense primer (50 pmol/µL) | 0.1 µL |
| probe (25 pmol/µL) | 0.1 µL |
| dNTP Mix (12.5 mM) | 0.3 µL |
| 10X PCR buffer (MgCl$_2$ included) | 1.5 µL |
| Taq-DNA polymerase | 0.75 U |
| PCR-grade H$_2$O | Add 15 µL |

Mixture 2 (Phosphorylated Hybridization Probe)
PCR Primer/Probe

```
L. monocytogenes sense primer
                                       (SEQ ID NO: 1)
(5'-CGC AAC AAA CTG AAG CAA AGG-3')

L. monocytogenes antisense primer
                                       (SEQ ID NO: 2)
(5'-BIOTIN-TCC GCG TGT TTC TTT TCG AT-3')

L. monocytogenes probe
                                       (SEQ ID NO: 4)
(5'-FITC-ATG CAT CTG CAT TCA ATA-Pho-3')
```

Reaction Mixture (Amplification/Hybridization)
Per Mixture:

| | |
|---|---|
| sense primer (50 pmol/µL) | 0.1 µL |
| antisense primer (50 pmol/µL) | 0.1 µL |
| probe (25 pmol/µL) | 0.1 µL |
| dNTP Mix (12.5 mM) | 0.3 µL |
| 10X PCR buffer (MgCl$_2$ included) | 1.5 µL |
| Taq-DNA polymerase | 0.75 U |
| PCR-grade H$_2$O | add 15 µl |

For testing, one negative sample (containing only PCR chemicals and H$_2$O) and one positive sample-containing additionally L. monocytogenes DNA (1.5 µL, total DIN concentration approximately 50 ng/µL)—from each mixture were used.

The PCR was performed in the SpeedCycler (Analytik Jena), using the rapid-cycler technology:

| Amplification/hybridization conditions | | | |
|---|---|---|---|
| Step 1 | Denaturing | 95° C. | 120 minutes |
| Step 2 | Amplification | | 37 cycles |
| | | 95° C. | 4 minutes |
| | | 55° C. | 4 minutes |
| | | 72° C. | 20 minutes |

| Amplification/hybridization conditions | | | |
|---|---|---|---|
| Step 3 | Denaturing | 95° C. | 300 minutes |
| Step 4 | Hybridization | 15° C. | 600 minutes |

The amplification event/the hybridization reaction was detected by means of gel-electrophoretic separation of the amplification/hybridization mixture (FIG. 1) as well as by means of lateral-flow test strips (GeneLine HybriDetect; Millenia Biotec GmbH; FIG. 2).

Comparison of the two figures demonstrates the disadvantages of the probe not protected from polymerase activity (mixture 1) and thus the unsuitability of the lateral-flow method in the case of probes without polymerization blocking. On the gel photograph, the negative control does not contain any specific DNA bands, whereas the test strip exhibits a strongly positive signal caused by doubly labeled primer dimers.

In contrast, the amplification mixture/hybridization mixture with the hybridization probe phosphorylated at the 3'-end exhibits only one positive signal, for the positive control, on the test strip. Thus, the result on the test strip correlates unambiguously with the gel photograph.

Figure 2:
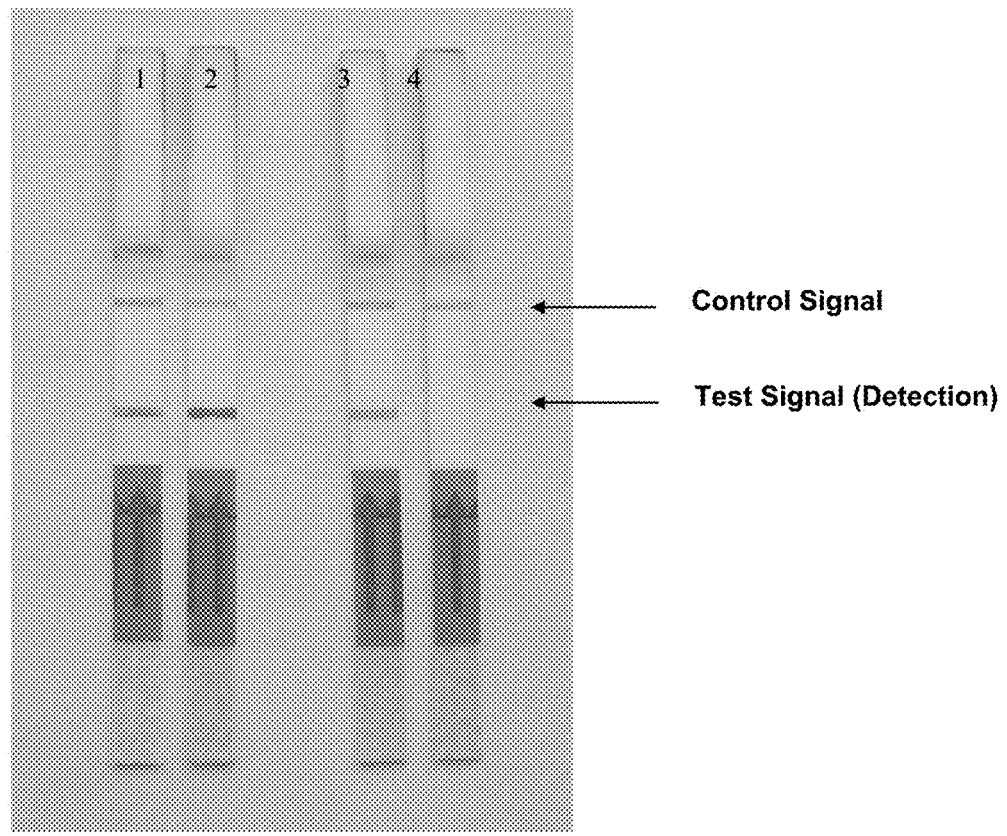
FIG. 2 shows the detection of the specific hybridization event on a lateral-flow test strip. Strip 1: positive control containing *L. monocytogense* DNA from mixture 1 containing sense primer, antisense primer, probe, dNTP Mix, 10×PCR buffer, Taq-DNA polymerase and PCR-grade $H_2O$; strip 2: negative control from mixture 1; strip 3: positive control containing *L. monocytogense* DNA from mixture 2 containing sense primer, antisense primer, probe, dNTP Mix, 10×PCR buffer, Taq-DNA polymerase and PCR-grade $H_2O$; strip 4: negative control from mixture 2.

Explanation of FIG. 1:
Lane 1: DNA ladder; lane 2: positive control from mixture 1; lane 3: negative control from mixture 1; lane 4: positive control from mixture 2; lane 5: negative control from mixture 2.

FIG. 2 shows the detection of the specific hybridization event on a lateral-flow test strip.

Explanation of FIG. 2:
Strip 1: positive control from mixture 1; strip 2: negative control from mixture 1; strip 3: positive control from mixture 2; strip 4: negative control from mixture 2.

Example 2

Performance of the Method by Means of Asymmetric PCR and Check of Specificity of the Test on the Basis of Testing of Positive and Negative Starting Samples The inventive method was used as an example for detection of *Rickettsia* DNA isolated from tick tissue. The specificity of the method was determined by means of parallel tests on *Rickettsia*-negative DNA samples, also isolated from tick tissue.

PCR Primer Probe:

```
Rickettsia sense primer:
                                       (SEQ ID NO: 5)
5'-GGG ACC TGC TCA CGG CGG-3'

Rickettsia antisense primer:
                                       (SEQ ID NO: 6)
5'-Biotin-TCT ATT GCT ATT TGT AAG AGC GGA TTG-3'

Rickettsia probe:
                                       (SEQ ID NO: 7)
5'-FITC-CAA AGA AGT ATT AAA GGA ACT C-Pho-3'
```

Reaction Mixture (Amplification/Hybridization)
Per Sample:

| | |
|---|---|
| sense primer (50 pmol/µL) | 0.05 µL |
| antisense primer (50 pmol/µL) | 0.1 µL |
| probe (25 pmol/µL) | 0.1 µL |

-continued

| | |
|---|---|
| dNTP Mix (12.5 mM) | 0.3 µL |
| 10X PCR buffer (MgCl$_2$ included) | 1.5 µL |
| Taq-DNA polymerase | 0.75 U |
| DNA (positive or negative) | 1.5 µL (approx. 50 ng) |
| PCR-grade H$_2$O | add 15 µl |

The PCR was performed in the SpeedCycler (Analytik Jena), using the rapid-cycler technology:

| Amplification/hybridization conditions | | | |
|---|---|---|---|
| Step 1 | Denaturing | 95° C. | 120 minutes |
| Step 2 | Amplification | | 37 cycles |
| | | 95° C. | 4 minutes |
| | | 55° C. | 4 minutes |
| | | 72° C. | 20 minutes |
| Step 3 | Denaturing | 95° C. | 300 minutes |
| Step 4 | Hybridization | 45° C. | 600 minutes |

Figure 3:
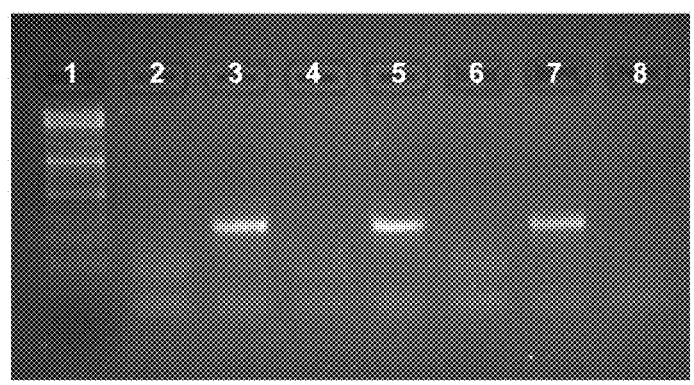
FIG. 3 shows that after completion of the coupled amplification/hybridization method, the specific detection of the exciting nucleic acid can be visualized by means of gel electrophoresis. Lane 1: DNA ladder; lane 2: negative sample; lane 3: positive sample containing *L. monocytogense* DNA; lane 4: negative sample; lane 5: positive sample containing *L. monocytogense* DNA; lane 6: negative sample; lane 7: positive sample; lane 8: PCR blank control.

After completion of the coupled amplification/hybridization method, the specific detection of the exciting nucleic acid was again visualized by means of a lateral-flow test strip (FIG. 4) as well as by means of gel electrophoresis (FIG. 3). The results show impressively the specific detection of the target nucleic acid to be detected. The entire process needed approximately 50 minutes.

Explanation of FIG. 3:
Lane 1: DNA ladder; lane 2: negative sample; lane 3: positive sample; lane 4: negative sample; lane 5: positive sample; lane 6: negative sample; lane 7: positive sample; lane 8: PCR blank control.

Figure 4:
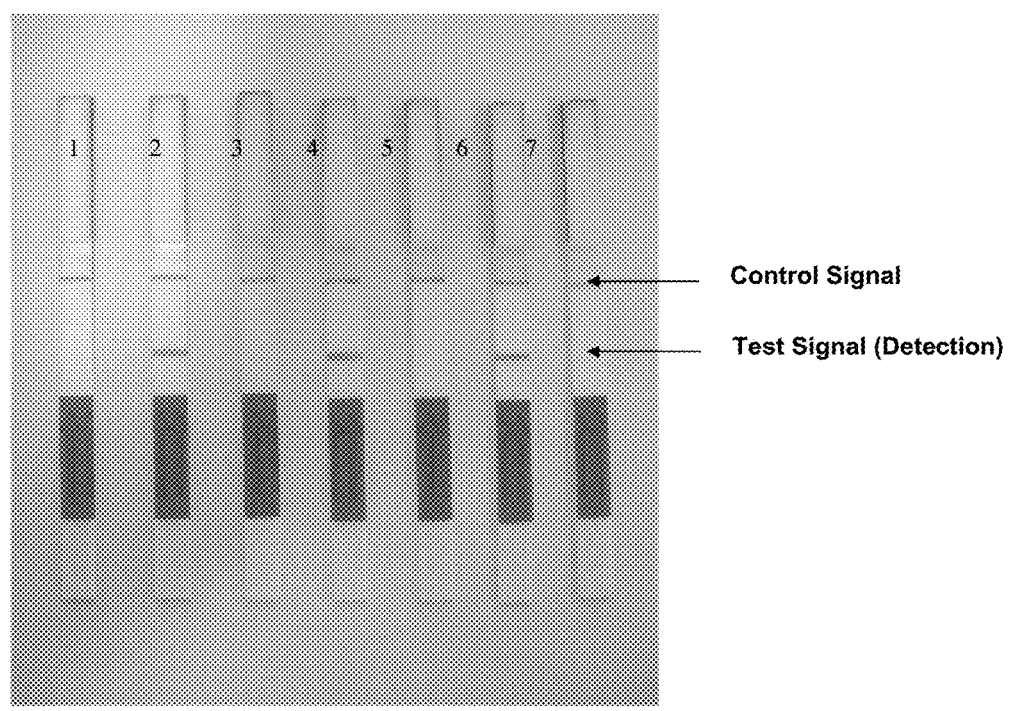
FIG. 4 shows that after completion of the coupled amplification/hybridization method, the specific detection of the exciting nucleic acid can be visualized by means of a lateral-flow test strip. Strip 1: negative sample; strip 2: positive sample containing *L. monocytogense* DNA; strip 3: negative sample; strip 4: positive sample containing *L. monocytogense* DNA; strip 5: negative sample; strip 6: positive sample containing *L. monocytogense* DNA; strip 8: PCR blank control.

FIG. 4 shows the detection of the specific hybridization events on a lateral-flow test strip.

Explanation of FIG. 4:
Strip 1: negative sample; strip 2: positive sample; strip 3: negative sample; strip 4: positive sample; strip 5: negative sample; strip 6: positive sample; strip 8: PCR blank control.

Various modifications and variations of the described nucleic acid products, compositions and methods as well as the concept of the invention will be apparent to those skilled in the art without departing from the scope and spirit of the invention. Although the invention has been described in connection with specific preferred embodiments, it should be understood that the invention as claimed is not intended to be limited to such specific embodiments. Various modifications of the described modes for carrying out the invention which are obvious to those skilled in the molecular biological, chemical, medical, biological, pharmacological arts or related fields are intended to be within the scope of the following claims.

Each document, patent application, or patent publication cited by or referred to in this disclosure is incorporated by reference in its entirety, especially of the material disclosed in the same paragraph or section surrounding the citation. Any patent document to which this application claims priority is also incorporated by reference in its entirety.

The invention claimed is:

1. A method for assaying at least one specific nucleic acid target sequence comprising:

amplifying a nucleic acid sequence to be assayed with at least one primer comprising a conjugate tag, if necessary, followed by strand separation, and hybridizing with at least one labeled signal generating hybridization probe completely or partly complementary to the target sequence, and detecting a hybridization reaction; wherein a) the amplification, and if necessary, the strand separation, and the hybridization take place in one reaction vessel, and b) the labeled signal generating hybridization probe hybridizes to the strand of the target sequence that contains the one primer comprising a conjugate tag and c) the detection of the hybridization reaction takes place on a solid phase outside the reaction vessel mentioned under a) and d) the solid phase contains a binding site for the conjugate tag of the one primer comprising a conjugate tag or for the labeled signal generating hybridization probe and thereby a hybridization product is thereby bound to the solid phase and e) the detection of the hybridization reaction takes place on a solid phase outside the reaction vessel mentioned under a) such that the solid phase has a binding site that permits binding with the conjugate of the one primer comprising a conjugate tag or with the label of the labeled signal generating hybridization probe, whereby the hybridization product is bound to the solid phase and detection of the bound hybridization product takes place by direct or indirect detection of a conjugate tag and/or label which is not amplified or hybridized or the conjugate tag of the one primer comprising a conjugate tag or the label of the labeled signal generating hybridization probe enters into binding with a detection molecule and then a conjugate tag and/or label which is not amplified or hybridized enters into binding with a binding site of the solid phase, whereby the hybridization product is bound to the solid phase and detection of the hybridization product bound to the solid phase takes place via the detection molecule and f) wherein in the labeled signal generating hybridization probe is blocked against the 5'→3' polymerase activity.

2. The method according to claim 1, wherein visualization or measurement of a PCR hybridization result takes place with an optical device.

3. The method according to claim 1, wherein the labeled signal generating hybridization probe is blocked against the 5'→3' polymerase activity by labeling or by phosphorylation.

4. The method according to claim 1, wherein the at least one primer comprising a conjugate tag is conjugated with biotin.

5. The method according to claim 1, wherein the labeled signal generating hybridization probe is labeled with fluorescein isothiocyanate.

6. The method according to claim 1, wherein said solid phase comprises a test strip that comprises a streptavidin binding site for coupling a biotin-labeled conjugate tag and a fluorescein isothiocyanate binding site for functional control of the test strip.

7. The method according to claim 6, wherein a PCR amplification mixture is mixed with a running buffer and applied on the test strip.

8. The method according to claim 6, wherein gold particles coated with anti-fluorescein isothiocyanate antibodies are located in a lower zone of the test strip, where a sample is applied, and in that the streptavidin binding site is located further along the test strip.

9. The method according to claim 1, wherein an asymmetric PCR is performed instead of the standard PCR reaction.

10. The method according to claim 1, wherein a reverse transcription takes place in the case of RNA assay before amplification.

11. A test kit for performing the method according to claim 1, comprising:

a reaction vessel for performing the amplification, the strand separation and the hybridization with the labeled signal generating hybridization probe, at least one primer comprising a conjugate tag, at least one labeled signal generating hybridization probe that is completely or partly complementary to the target sequence, that is blocked against the 5'→3' polymerase activity and is optionally provided with a label, and that hybridizes to the strand of the target sequence that contains the primer comprising a conjugate tag, at least one solid phase, which contains a binding site for the conjugate tag and/or label either of the primer comprising a conjugate tag or of the labeled signal generating hybridization probe, and/or PCR reagents as well as at least one running agent for detection of hybridization.

12. The test kit according to claim 11, wherein the reaction vessel contains the primer comprising a conjugate tag, the probe and the PCR reagents known in themselves in solid form.

13. The method of claim 1, which is a qualitative method for detecting the target sequence.

14. The method according to claim 1 that is a rapid test in which detection takes less than one hour.

15. The method according to claim 1 that is a rapid test that comprises multiplex detection, wherein several primers comprising a conjugate tag and labeled signal generating hybridization probes labeled by either identical or different molecules are employed.

16. The method according to claim 1, wherein the target sequence is from a virus or a bacterium.

17. A method for food diagnosis, environmental analysis, or hospital hygiene comprising the method of claim 1.

18. The method according to claim 1, wherein the target sequence is from *Salmonella, Listeria, E. coli, Campylobacter, Shigella, Enterobacter*, MRSA microbes or *Legionella*.

19. The method according to claim 1, wherein the target sequence is from *Borrelia, Rickettsia, Erlichia, Babesia*, or another tick-born pathogen.

20. The method according to claim 1, wherein said target sequence comprises a SNP, mutation or methylated sequence motif.

21. A method for detecting a target nucleic acid comprising:

conducting a polymerase chain reaction (PCR) on a sample suspected of containing the target nucleic acid in a PCR reaction mixture comprising:

two PCR primers suitable for amplifying the target nucleic acid, one of which comprises a conjugate tag at its 5' end, and a labeled signal generating hybridization probe which is able to hybridize to the strand of the target nucleic acid containing the sequence of primer comprising a conjugate tag at its 5' end, but which is blocked against the 5'→3' polymerase activity and has been chemically modified so that it is not elongated by a 5'→3' polymerase used for the PCR;

denaturing the PCR reaction mixture at a temperature sufficient to separate the strands of a PCR amplification product generated by the PCR, cooling the denatured PCR reaction mixture to a hybridization temperature of the labeled signal generating hybridization probe for a time and under conditions sufficient for the labeled signal generating hybridization probe to bind to the complementary strand of the nucleic acid amplification product, and contacting the resulting mixture with a solid phase support comprising a nucleic acid complementary to the PCR probe;

wherein the occurrence of, or amount of, binding to the solid phase support compared to a control indicates the presence of the target nucleic acid in the sample.

22. The method of claim 21, Therein contacting the resulting mixture with a solid phase support comprising a nucleic acid complementary to the PCR probe is conducted outside of a reaction vessel used to perform amplification and hybridization.

23. The method of claim 22, wherein said solid phase is a lateral-flow test strip.

* * * * *

SEQUENCE LISTING

<160> NUMBER OF SEQ ID NOS: 7

<210> SEQ ID NO 1
<211> LENGTH: 21
<212> TYPE: DNA
<213> ORGANISM: Listeria monocytogenes

<400> SEQUENCE: 1
cgcaacaaac tgaagcaaag g         21

<210> SEQ ID NO 2
<211> LENGTH: 20
<212> TYPE: DNA
<213> ORGANISM: Listeria monocytogenes
<220> FEATURE:
<221> NAME/KEY: modified_base
<222> LOCATION: (1)..(1)
<223> OTHER INFORMATION: 5'-biotin-T

<400> SEQUENCE: 2
tccgcgtgtt tcttttcgat           20

<210> SEQ ID NO 3
<211> LENGTH: 20
<212> TYPE: DNA
<213> ORGANISM: Listeria monocytogenes
<220> FEATURE:
<221> NAME/KEY: modified_base
<222> LOCATION: (1)..(1)
<223> OTHER INFORMATION: 5'-FITC-C

<400> SEQUENCE: 3
ccatggcacc accagcatct           20

<210> SEQ ID NO 4

-continued

```
<211> LENGTH: 18
<212> TYPE: DNA
<213> ORGANISM: Listeria monocytogenes
<220> FEATURE:
<221> NAME/KEY: modified_base
<222> LOCATION: (1)..(1)
<223> OTHER INFORMATION: 5'-FITC-a
<220> FEATURE:
<221> NAME/KEY: modified_base
<222> LOCATION: (18)..(18)
<223> OTHER INFORMATION: a-PHO-3'

<400> SEQUENCE: 4
atgcatctgc attcaata                                                 18

<210> SEQ ID NO 5
<211> LENGTH: 18
<212> TYPE: DNA
<213> ORGANISM: Rickettsia sp.

<400> SEQUENCE: 5
gggacctgct cacggcgg                                                 18

<210> SEQ ID NO 6
<211> LENGTH: 27
<212> TYPE: DNA
<213> ORGANISM: Rickettsia sp.
<220> FEATURE:
<221> NAME/KEY: modified_base
<222> LOCATION: (1)..(1)
<223> OTHER INFORMATION: 5'-biotin-t

<400> SEQUENCE: 6
tctattgcta tttgtaagag cggattg                                       27

<210> SEQ ID NO 7
<211> LENGTH: 22
<212> TYPE: DNA
<213> ORGANISM: Rickettsia sp.
<220> FEATURE:
<221> NAME/KEY: modified_base
<222> LOCATION: (1)..(1)
<223> OTHER INFORMATION: 5'-FITC-c
<220> FEATURE:
<221> NAME/KEY: modified_base
<222> LOCATION: (22)..(22)
<223> OTHER INFORMATION: c-PHO-3'

<400> SEQUENCE: 7
caaagaagta ttaaaggaac tc                                            22
```